United States Patent [19]

Colle

[11] 3,969,400
[45] July 13, 1976

[54] CONTINUOUS PROCESS FOR DRYING SODIUM VINYL-SULFONATE

[75] Inventor: Jan Colle, Oostende, Belgium

[73] Assignee: U.C.B., Société Anonyme, Brussels, Belgium

[22] Filed: Jan. 9, 1975

[21] Appl. No.: 539,933

[30] Foreign Application Priority Data
Jan. 25, 1974 United Kingdom.................. 3492/74

[52] U.S. Cl............................................. 260/513 R
[51] Int. Cl.$^2$........................................ C07C 143/16
[58] Field of Search ...................... 260/513 R, 513 T

[56] References Cited
UNITED STATES PATENTS

| | | | |
|---|---|---|---|
| 2,597,696 | 5/1952 | Anthes et al..................... | 260/513 R |
| 3,243,454 | 3/1966 | Klass et al....................... | 260/513 R |
| 3,312,735 | 4/1967 | Medford et al. ................ | 260/513 T |
| 3,872,165 | 3/1975 | Schenk et al. .................. | 260/513 R |

Primary Examiner—James O. Thomas, Jr.
Assistant Examiner—Nicky Chan
Attorney, Agent, or Firm—Wenderoth, Lind & Ponack

[57] ABSTRACT

Continuous process for the preparation of dry and storage-stable sodium vinyl sulfonate which comprises a. adding, in a first stage, an alkali metal hydroxide to the starting aqueous solution of sodium vinyl-sulfonate in an amount such that the solution contains from 40 to 300 mg. of alkaline metal hydroxide per 100 g. of sodium vinyl-sulfonate, b. concentrating the resulting alkaline solution by evaporation in a second stage at a temperature of from 50° to 100°C. at a pressure of from 40 to 200 mm.Hg. to give an aqueous solution having a sodium vinyl-sulfonate concentration of from 40 to 55% by weight and c. in a third stage, subjecting the resulting concentrated solution to drying at a temperature of from 50° to 100°C. at a pressure of from 40 to 200 mm.Hg. to give solid sodium vinyl-sulfonate, the water content of which is, at most, 2% by weight.

5 Claims, No Drawings

CONTINUOUS PROCESS FOR DRYING SODIUM VINYL-SULFONATE

The present invention is concerned with a continuous process for drying sodium vinyl-sulfonate.

Sodium vinyl-sulfonate is a polymerizable organic compound which has many industrial uses, particularly as an antistatic agent and as an agent improving the tinctorial affinity of synthetic fibres, such as polyacrylonitrile and polypropylene, to cationic dyes, as a dispersing agent in polymer emulsions, as a wetting agent for lowering the mixing water content of cement, as a starting material for the production of cation exchange resins and synthetic rubber and the like.

Sodium vinyl-sulfonate is produced industrially in the form of aqueous solutions with a concentration of about 25 to 35% and it is generally in that form that it is marketed. Nevertheless, particularly for the transport of this product over long distances, it would be much more advantageous to obtain it in the form of far more concentrated aqueous solutions or even as a dry product. But, numerous difficulties are encountered because of the particular chemical and physical properties of this compound. From the chemical point of view, sodium vinylsulfonate has, on the one hand, a great tendency to polymerize and, on the other hand, to be converted into sodium 2-hydroxy-ethanesulfonate by the addition of water to the vinyl double bond. From the physicl point of view, sodium vinyl-sulfonate has adhesive properties which are the more pronounced the higher is its concentration in aqueous solution, thus leading to the clogging of the heating surfaces used in conventional concentration and/or drying apparatus.

Belgian Patent Specification No. 780,701 describes a process for producing highly concentrated or dry sodium vinyl-sulfonate, wherein the evaporation of the water of dissolution is carried out at atmospheric pressure at temperatures between 40° and 70°C. with the use of a hot, turbulent gas current. For this purpose, the amount of solution treated is from 10 to 100 times the amount of water which can be evaporated under the temperature conditions indicated above. Therefore, the solution treated has to be passed several times through the evaporator in order to obtain the desired degree of concentration. The apparatus used is an atomization tower which, in Example 1 of this Belgian Patent Specification has a diameter of 3.2 meters and a height of 8 meters for the treatment of 175 kg. per hour of an aqueous vinyl-sulfonate solution containing 60% of water.

There are two disadvantages of the process described in this Belgian Patent Specification: on the one hand, a high consumption of thermal and mechanical energy resulting from repeated recycling and, on the other hand, large dimensions of the apparatus for a relatively modest production rate.

Contrary to the teachings of this Belgian Patent Specification, according to which "sodium vinyl-sulfonate does not tolerate heat treatment in a kettle equipped with an agitator at temperatures higher than 40°C. in an alkaline aqueous solution" I have now developed a continuous process for drying sodium vinyl-sulfonate in which the operation is carried out in an alkaline medium at temperatures higher than 40°C. while, nevertheless, obtaining a product of better quality than that which would be obtained by operating in a neutral or acid medium.

According to the present invention, the unexpected discovery has been made that it is possible to obtain substantially dry sodium vinyl-sulfonate of excellent quality and with good storage stability by a continuous process which comprises (a) adding, in a first stage, an alkali metal hydroxide to the aqueous solution of sodium vinyl-sulfonate coming from the manufacturing process in an amount such that the solution contains from 40 to 300 mg. of alkali metal hydroxide per 100 g. of sodium vinyl-sulfonate, (b) concentrating the resulting alkaline solution by evaporation in a second stage at a temperature of from 50° to 100°C. at a pressure of from 40 to 200 mm.Hg. to give an aqueous solution having a sodium vinyl-sulfonate concentration of from 40 to 55% by weight and (c) in a third stage, subjecting the resulting concentrated aqueous solution to drying at a temperature of from 50° to 100°C. at a pressure of from 40 to 200 mm.Hg. to give solid sodium vinyl-sulfonate, the water content of which is, at most, 2% by weight.

In stage (a) of the process of the present invention, the aqueous solution of sodium vinyl-sulfonate coming from the manufacturing process generally contains from 25 to 35% by weight of pure sodium vinyl-sulfonate, together with more or less considerable amounts of impurities, such as sodium 2-hydroxy-ethanesulfonate, sodium sulfate and sodium chloride. Nevertheless, this sodium vinyl-sulfonate content is not critical for the process of the present ivention since it is possible to start with an aqueous solution having any concentration of this compound, for example 10 to 40% by weight. In the course of my investigations, I have found that the sodium vinyl-sulfonate solution is progressively acidified in the course of its concentration by evaporation and that the dry product obtained in this manner has a very poor storage stability, which results in a considerable decrease of its sodium vinyl-sulfonate titre. In order to compensate for this consumption of alkali, according to the present invention, a slight excess of alkali metal hydroxide is added to the aqueous solution of the vinyl-sulfonate before it is subjected to the concentration process, this excess of alkali metal hydroxide being from 40 to 300 mg. per 100 g. of sodium vinyl-sulfonate present in the solution so that the substantially dry sodium vinyl-sulfonate obtained at the end of the continuous process of the present invention will contain about 20 to 100 mg. of alkali metal hydroxide per 100 g. of sodium vinyl-sulfonate. It would be possible to add a still larger amount of alkali but this is not advisable because the final product would contain an unnecessarily higher content of free alkali.

By alkali metal hydroxide, there is to be understood, in the present specification, sodium or potassium hydroxide and preferably sodium hydroxide.

In stage (b) of the process of the present invention, the slightly alkaline solution of sodium vinyl-sulfonate obtained at the end of stage (a) is subjected to partial dehydration so as to obtain an aqueous solution containing from 40 to 55% by weight of sodium vinyl-sulfonate, operating within a temperature range of 50 to 100°C. and with an absolute pressure of 40 to 200 mm.Hg. This operation is preferably carried out continuously in any evaporator apparatus making it possible to obtain the above-mentioned concentration of sodium vinyl-sulfonate.

For the efficient carrying out of the operation, it is important not to exceed the specified upper concentration limit in order to avoid the deposition of solid material on the heat exchange surfaces of the evaporator used for the process. An evaporator apparatus which is particularly suitable for this stage of the process of the present invention is a thin layer evaporator because of the possibility of carrying out the concentration continuously, its small dimensions and its very high hourly production rate.

In stage (c) of the process of the present invention, the concentrated aqueous solution of sodium vinyl-sulfonate obtained at the end of stage (b) is converted, by a continuous process, into a substantially dry product, the water content of which is at most 2% by weight. For this purpose, the solution is heated at a temperature of 50° to 100°C. at an absolute pressure of from 40 to 200 mm.Hg. in a continuously operating drying apparatus. Whereas in Example 1 of the above-mentioned Belgian Patent Specification No. 780,701, it is said to be inadvisable to use a double drum dryer, since otherwise a considerably degraded product would be obtained, I have, surprisingly, found that dryer of this type can be successfully used for carrying out stage (c) of the present invention, without any decrease in quality of the product obtained being found. Utilizing an apparatus of this king, there was, indeed, obtained a dry sodium vinyl-sulfonate in powder and/or flake form which is easily and completely re-dissolved in water, even at ambient temperature, and which has an excellent storage stability, provided that the usual precautions for the storage of materials sensitive to light and humidity are observed, for example, storage in fibre drums with a polythene liner in a dry place. The performance of stage (c) of the present invention is, nevertheless, not limited to any particular type of apparatus; any continuous apparatus, in which the temperature and pressure conditions specified above can be applied, may be used for this purpose.

The advantages of the process according to the present invention are as follows:

the process is continuous;

it provides a substantially dry product (water content less than 2%) which has excellent storage properties and which the user can reconvert, when desired, into aqueous solutions of any concentration;

it is carried out in conventional apparatus of small dimensions, with a high output rate and with great operating safety;

the apparatus for carrying out the process is perfectly suitable for complete automation, thus ensuring great physical and chemical homogeneity of the product obtained;

finally, it is very economical, both from the point of view of the investment required and from the point of view of operating costs.

The following Examples are given for the purpose of illustrating the present invention:

EXAMPLE 1

Use is made of a rotary laboratory evaporator comprising a 1 liter glass flask rotating in a water bath, the heating of which is controlled by a thermostat and which is connected to a vacuum pump.

An aqueous solution of sodium vinyl-sulfonate (SVS), which is to be converted into a practically dry powder, has the following composition:

| SVS | 29.6% by weight |
| Na$_2$SO$_4$ | 0.76% by weight |
| water | 60.30% by weight |
| other salts (by difference) | 9.34% by weight |

The "other salts" are composed principally of sodium 2-hydroxyethanesulfonate.

Three parallel tests are carried out, for which each time the SVS solution described above is used:

Test 1.1: 500 g. of this solution.

Test 1.2: 500 g. of this solution to which are added 4.5 ml. 0.5N sodium hydroxide solution (i.e. 60.8 mg. of NaOH per 100 g. of SVS)

Test 1.3: 500 g. of this solution to which are added 4.5 ml. 0.5N potassium hydroxide solution (i.e. 86.5 mg. of KOH per 100 g. of SVS).

In each of the tests, the solution is introduced into the rotary flask and a vacuum of 100 mm.Hg. is applied to the system. The temperature of the water bath is progressively raised to 70°C., while rotating the flask; the water dissolving the SVS and the various other components is eliminated by distillation and, consequently, the composition in the flask becomes more and more pasty. When agitation no longer takes place uniformly, the operation is stopped and the composition is broken up into small pieces by means of a spatula, whereupon the dehydration operation is repeated under the same conditions as above. When the composition has become pulverulent, the pressure is decreased to 45 mm.Hg. and the temperature of the water-bath increased to 90°C. In the three tests, there are thus obtained about 185 g. of a powder having the following analyses (percentages being expressed by weight):

|  |  | Test 1.1 | Test 1.2 | Test 1.3 |
| --- | --- | --- | --- | --- |
| SVS | (%) | 72.35 | 74.3 | 73.65 |
| Na$_2$SO$_4$ | (%) | 1.95 | 1.9 | 1.87 |
| water | (%) | 1.20 | 1.5 | 1.35 |
| other salts (by difference) | (%) | 24.50 | 22.26 | 23.07 |
| NaOH | (%) | — | 0.034 | — |
| KOH | (%) | — | — | 0.059 |

The storage stability of the SVS powders obtained in this manner is then checked. For this purpose, each powder is stored in a well-stoppered, brown glass bottle away from light and the course of the SVS titre of the powder is followed ove the course of time. The following results (in % by weight) are thus obtained:

| Storage time | Test 1.1 | Test 1.2 | Test 1.3 |
| --- | --- | --- | --- |
| 15 days | 69.2 | 74.25 | 73.63 |
| 1 month | 65.35 | 74.31 | 73.63 |
| 2 months | 59.47 | 74.27 | 73.61 |
| 3 months | 55.6 | 74.25 | 73.58 |
| 6 months | 52.73 | 73.97 | 73.29 |
| 1 year | 47.58 | 73.58 | 73.16 |

These tests show the effectiveness of adding an alkali metal hydroxide upon the storage stability of sodium vinyl-sulfonate in powder form.

EXAMPLE 2

The aqueous solution of SVS to be concentrated has the following composition:

| SVS | 28.7% by weight |
| Na$_2$SO$_4$ | 0.83% by weight |
| water | 58.75% by weight |

-continued

| | |
|---|---|
| other salts (by difference) | 11.72% by weight |

To 500 g. of this solution are added 7 ml. 0.5N sodium hydroxide solution (i.e. 97.56 mg. of NaOH per 100 g. of SVS) and the solution is treated in the same apparatus as used in Example 1.

The mode of operation of Example 1 is modified by applying a vacuum of 200 mm.Hg., while the temperature of the water in the water-bath is brought to 90°C. When the mixture becomes too pasty, the composition is broken up and the drying operation is terminated, while maintaining the same conditions of temperature and pressure.

There are thus obtained 197.3 g. of a powder having the following composition (in % by weight):

| | |
|---|---|
| SVS | 68.65 |
| $Na_2SO_4$ | 1.98 |
| water | 1.35 |
| NaOH | 0.053 |
| other salts (by difference) | 27.967 |

After storage for 6 months in a carefully stoppered brown glass bottle away from light, the product still has a titre of 68.57% by weight of SVS.

EXAMPLE 3

In this Example, use is made of an aqueous solution of SVS which has the following composition (in % by weight):

| | |
|---|---|
| SVS | 34.85 |
| $Na_2SO_4$ | 0.73 |
| water | 62.00 |
| other salts (by difference) | 2.42 |

For test 3.1, use is simply made of 500 g. of this solution, while for test 3.2 there are added to 500 g. of this solution 8.7 ml. 0.5N sodium hydroxide solution (i.e. 100 mg. of NaOH per 100 g. of SVS). These two solutions are dried in accordance with the conditions given in Example 1.

In both cases, there are obtained 183 g. of dry powder having the following composition (in % by weight):

| | Test 3.1 | Test 3.2 |
|---|---|---|
| SVS | 90.49 | 90.63 |
| $Na_2SO_4$ | 1.92 | 1.87 |
| NaOH | — | 0.084 |
| water | 1.3 | 1.2 |
| other salts (by difference) | 6.29 | 6.216 |

Storage stability (% by weight of SVS):

| after | Test 3.1 | Test 3.2 |
|---|---|---|
| 1 month | 85.34 | 90.61 |
| 2 months | 81.22 | 90.60 |
| 3 months | 78.17 | 90.60 |
| 6 months | 75.83 | 90.53 |

EXAMPLE 4

This Example illustrates the carrying out of the process of the present invention on a pilot scale. The starting aqueous solution, fed continuously from the manufacturing installation, has the following composition (in % by weight):

| | |
|---|---|
| SVS | 30.2 |
| $Na_2SO_4$ | 0.82 |
| water | 57.66 |
| other salts (by difference) | 11.32 |

Density of solution at 20°C.: 1.245.

The solution is first continuously introduced into a vat containing an agitator and to which there are added, by means of a metering pump, 0.83 kg. of an aqueous solution of sodium hydroxide (31.5% by weight) per 1000 liters of SVS solution. The solution thus contains 69.53 mg. of NaOH per 100 g. of SVS.

From this vat, the SVS solution is continuously supplied to a thin layer evaporator. The latter has a heat exchange surface of 1 square meter; it is heated with steam and is connected to a vacuum source. The conditions of operation are as follows:

heating steam pressure: 2.2 kg/cm$^2$ absolute pressure prevailing in the system: 60 mm.Hg.

rate of feed of SVS solution: 290 liters/hour, i.e. about 361 kg./hour.

At the outlet of the evaporator, the SVS solution has the following composition:

| | | |
|---|---|---|
| SVS | 45.29% | (by weight) |
| $Na_2SO_4$ | 1.23% | (by weight) |
| NaOH | 0.031% | (by weight) |
| water | 36.51% | (by weight) |
| other salts (by difference) | 16.939% | (by weight) |

Thus, the concentration operation permitted the evaporation of about 120 kg. of water per hour.

The concentrate thus obtained is continuously fed to a double drum drier connected to a vacuum source. Each of the drums has a length of 1200 mm. and a diameter of 500 mm.; they are heated with steam and scraped by a set of knives to remove dry product from their surface. The conditions of operation of the drier are as follows:

drums heating steam pressure: 1.2 kg/cm$^2$ absolute pressure prevailing in the system: 45 mm.Hg.

speed of rotation of drums: 7 revolutions per minute.

The product obtained falls into a cylindrical afterdrier having a horizontal axis and heated by steam at 1.0 kg./cm$^2$, the drier being equipped with scrapers which move the product towards a discharge aperture, from which the dry, pulverulent product falls into a truck. The final product, discharged at a temperature of 90°C., has the following composition (in % by weight):

| | |
|---|---|
| SVS | 70.63 |
| $Na_2SO_4$ | 1.91 |
| NaOH | 0.045 |
| water | 1.25 |
| other salts (by difference) | 26.165 |

The output per hour of the installation is 147 kg.

This product is stored in fibre drums lines with polyethylene. After storage for 6 months, it still has an SVS titre of 70.49% by weight.

I claim:

1. A continuous process for preparing dry and storage stable sodium vinyl-sulfonate from an aqueous solution thereof, which comprises (a) adding, in a first stage, an alkali metal hydroxide to the starting aqueous solution of sodium vinyl-sulfonate in an amount such that the solution contains from 40 to 300 mg. of sodium or potassium hydroxide per 100 g. of sodium vinyl-sulfonate, (b) concentrating the resulting alkaline solution by evaporation in a second stage at a temperature of from 50° to 100°C. at a pressure of from 40 to 200 mm.Hg. to give an aqueous solution having a sodium vinyl-sulfonate concentration of from 40 to 55% by weight and (c) in a third stage, subjecting the resulting concentrated solution to drying at a temperature of from 50° to 100°C. at a pressure of from 40 to 200 mm.Hg. to give solid sodium vinyl-sulfonate, the water content of which is, at most, 2 % by weight.

2. The process according to claim 1, wherein the starting aqueous solution of sodium vinyl-sulfonate contains from 10 to 40% by weight of sodium vinyl-sulfonate.

3. The process according to claim 1, wherein the starting aqueous solution of sodium vinyl-sulfonate contains from 25 to 35% by weight of sodium vinyl-sulfonate.

4. The process according to claim 1, wherein the second stage is carried out in a thin layer evaporator.

5. The process according to claim 1, wherein the third stage is carried out in a double drum dryer.

* * * * *